United States Patent
Chow et al.

(10) Patent No.: US 8,672,985 B2
(45) Date of Patent: Mar. 18, 2014

(54) BONE FASTENERS AND METHOD FOR STABILIZING VERTEBRAL BONE FACETS USING THE BONE FASTENERS

(75) Inventors: David Chow, West Chester, PA (US); Perry Geremakis, Manalapan, NJ (US); Erik O. Martz, Savage, MN (US); Stephen Howard Hochschuler, Scottsdale, AZ (US); Daniel E. Rosenthal, Short Hills, NJ (US); Steven Annunziato, Center Valley, PA (US); Larry C. Johnston, Jackson, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 526 days.

(21) Appl. No.: 12/914,130

(22) Filed: Oct. 28, 2010

(65) Prior Publication Data

US 2011/0046679 A1 Feb. 24, 2011

Related U.S. Application Data

(62) Division of application No. 10/500,395, filed as application No. PCT/US02/41444 on Dec. 27, 2002, now Pat. No. 7,833,255.

(60) Provisional application No. 60/343,810, filed on Dec. 27, 2001.

(51) Int. Cl.
*A61B 17/86* (2006.01)

(52) U.S. Cl.
USPC ............ 606/301; 606/300; 606/310; 606/313

(58) Field of Classification Search
USPC .......................... 606/300–321; 411/340, 345
See application file for complete search history.

(56) References Cited

U.S. PATENT DOCUMENTS

| 681,028 | A | | 8/1901 | Lehmann |
| 2,077,804 | A | * | 4/1937 | Morrison ..................... 606/68 |
| 2,485,531 | A | | 10/1949 | King et al. |
| 2,511,051 | A | | 6/1950 | Dzus |
| 3,678,535 | A | | 7/1972 | Charles |
| 3,739,773 | A | | 6/1973 | Schmitt et al. |
| 4,430,760 | A | | 2/1984 | Smestad |
| 4,440,750 | A | | 4/1984 | Glowacki et al. |
| 4,472,840 | A | | 9/1984 | Jefferies |
| 4,627,853 | A | | 12/1986 | Campbell et al. |

(Continued)

FOREIGN PATENT DOCUMENTS

| EP | 0 413 492 A2 | 2/1991 |
| EP | 0 495 284 A1 | 7/1992 |

(Continued)

OTHER PUBLICATIONS

Glowacki et al., "Application of the Biological Principle of Induced Osteogenesis for Craniofacial Defects", *The Lancet*, vol. 1, No. 8227, pp. 959-962, May 2, 1981.

(Continued)

*Primary Examiner* — Nicholas Woodall
(74) *Attorney, Agent, or Firm* — Sorell Lenna & Schmidt LLP

(57) ABSTRACT

A bone fastener for stabilizing bone fragments includes a single or multiple components coupleable with one another and displaceable to a locked position of the bone fastener.

5 Claims, 15 Drawing Sheets

(56) References Cited

U.S. PATENT DOCUMENTS

| | | |
|---|---|---|
| 4,824,939 A | 4/1989 | Simpson |
| 4,932,973 A | 6/1990 | Gendler |
| 5,001,169 A | 3/1991 | Nathan et al. |
| 5,053,049 A | 10/1991 | Campbell |
| 5,073,373 A | 12/1991 | O'Leary et al. |
| 5,092,887 A | 3/1992 | Gendler |
| 5,098,433 A * | 3/1992 | Freedland ................. 606/63 |
| 5,112,354 A | 5/1992 | Sires |
| 5,290,558 A | 3/1994 | O'Leary et al. |
| 5,298,254 A | 3/1994 | Prewett et al. |
| 5,306,304 A | 4/1994 | Gendler |
| 5,314,476 A | 5/1994 | Prewett et al. |
| 5,507,813 A | 4/1996 | Dowd et al. |
| 5,510,396 A | 4/1996 | Prewett et al. |
| 5,707,373 A | 1/1998 | Sevrain et al. |
| 5,797,919 A | 8/1998 | Brinson |
| 5,919,194 A | 7/1999 | Anderson |
| 6,099,527 A | 8/2000 | Hochschuler et al. |
| 6,158,437 A | 12/2000 | Vagley |
| 6,200,330 B1 | 3/2001 | Benderev et al. |
| 6,258,091 B1 | 7/2001 | Sevrain et al. |
| 6,302,887 B1 | 10/2001 | Spranza et al. |
| 6,315,780 B1 | 11/2001 | Lalonde |
| 6,470,709 B1 | 10/2002 | Siekierski |
| 6,569,168 B2 | 5/2003 | Lin |
| 6,663,653 B2 | 12/2003 | Akerfeldt |
| 6,666,866 B2 | 12/2003 | Martz et al. |
| 6,746,454 B2 | 6/2004 | Winterbottom et al. |
| 6,911,045 B2 | 6/2005 | Shimp |
| 2001/0011173 A1 | 8/2001 | Lerch |
| 2003/0078585 A1 | 4/2003 | Johnson et al. |
| 2003/0130667 A1 | 7/2003 | Lin |
| 2004/0098129 A1 | 5/2004 | Lin |
| 2004/0162562 A1 | 8/2004 | Martz |
| 2004/0243242 A1 | 12/2004 | Sybert et al. |
| 2004/0249377 A1 | 12/2004 | Kaes et al. |
| 2005/0038511 A1 | 2/2005 | Martz et al. |
| 2005/0251146 A1 | 11/2005 | Martz et al. |
| 2006/0095043 A1 | 5/2006 | Martz et al. |
| 2006/0149376 A1 | 7/2006 | Shimp et al. |
| 2007/0073293 A1 | 3/2007 | Martz et al. |

FOREIGN PATENT DOCUMENTS

| | | |
|---|---|---|
| EP | 0 555 807 A1 | 8/1993 |
| EP | 0 419 275 B1 | 1/1995 |
| EP | 0 483 944 B1 | 7/1995 |
| GB | 2 175 807 A | 12/1986 |

OTHER PUBLICATIONS

Kiviranta et al., "The Rate of Calcium Extraction During EDTA Decalcification from Thin Bone Slices as Assessed with Atomic Absorption Spectrophotometry", *Histochemistry 68*, pp. 119-127, 1980.

Covey et al., "Clinical Induction of Bone Repair With Demineralized Bone Matrix or a Bone Morphogenetic Protein", *Orthopaedic Review*, vol. XVIII, No. 8, pp. 857-863 (Aug. 1989).

Habal et al., "Autologous Corticocancellous Bone Paste for Long Bone Discontinuity Defects: An Experimental Approach", *Annals of Plastic Surgery*, vol. 15, No. 2, pp. 138-142, (Aug. 1985).

\* cited by examiner

BONE FASTENERS AND METHOD FOR STABILIZING VERTEBRAL BONE FACETS USING THE BONE FASTENERS

CROSS-REFERENCE TO RELATED APPLICATION

This application is a divisional of U.S. application Ser. No. 10/500,395, which is a 371 national stage entry of PCT/US2002/041444 filed Dec. 27, 2002, which claims priority to U.S. Provisional Application 60/343,810 filed Dec. 27, 2001, the contents of all of which are hereby incorporated in their entirety by reference.

BACKGROUND

1. Technical Field

The present disclosure relates to bone fastener. In particular, the present invention relates to a series of bone fasteners for use in stabilizing a pair of adjacent vertebral facets to one another and to a method of operating the inventive bone fasteners.

2. Background of Related Art

It is often necessary to fix the facet joints of adjacent vertebrae to one another or to attach objects (e.g., bone plates, bone grafts, etc.) to a bone itself. For example, in repairing a fractured or damaged vertebra, it is often necessary to stabilize individual vertebrae in order to promote proper healing. Stabilization is often accomplished by fixing one vertebra to adjacent vertebrae or by using a bone plate, or pedicle screw and rod system, to interconnect adjacent or a series of vertebrae to one another.

Prior art techniques often utilize screws to secure vertebrae or bone to one another or to secure a plate and/or rods between individual vertebrae or between individual bones. In order to more securely anchor a screw into the vertebrae, bicortical placement of the screw into the bone is recommended. In other words, the screw is to penetrate through the cortex layer that is adjacent to the bone plate which is to be attached, then penetrate through the cancellous tissue in the interior of the bone and finally, penetrate into the opposite cortex layer on the opposite side of the bone.

Entering a bone is an invasive procedure that sometimes, based on the severity of problem which is encountered by an operating surgeon, requires that a screw penetrate through the opposite cortex layers. Accordingly, known screws have an elongated structure capable of bicortical purchase, otherwise the screws may loosen and fail to securely couple the plate to the bone or vertebrae.

Another known method is the use of pedicle screws for, stabilizing adjacent vertebrae as well as for monosegmental or multisegmental fixation of a spinal column. Such screws typically do not obtain bi-cortical purchase and are therefore more susceptible to loosening. To help reduce this risk, the longest and largest size screw that can be safely inserted into the dense cancellous bone of the pedicle is used to maximize bone purchase. A typical pedicle screw includes a threaded portion and a receiver portion rigidly connected thereto at the head end of the screw. In use, several pairs of such screws are threaded into the vertebral bodies of the adjacent vertebra on either side of the spinal column through the pedicles. The respective receiver portions comprise receiving slits wherein a respective rod is passed through these receiving slits in the right and left hand group of pedicle screws. Thereafter, the rod is fixed to the respective receiver portion by means of fastening devices.

It is a drawback of this solution that it is difficult to rigidly insert screws through the pedicles on into the vertebral bodies and at the same time position the pedicle screws in two planes in exactly such a manner that the axes of the receiving slits in the receiver parts in the vertical columns align such that the rod may be passed through the receiving slits without distortion of the screws. Even with the advent of polyaxial screws, alignment of the receiving slits and contouring the rods to fit these slits remain a time consuming process. A further drawback is the difficulty improperly positioning the screws within the pedicles. This takes much skill on the part of the surgeon. Compromising the integrity of the cortical walls of the pedicle as well as further penetration into the vertebral body of the vertebra could lead to neurological complications and eventual implant loosening. Additionally, the implantation of a pedicle screw system is a very invasive procedure, whereby a large incision is made to expose multiple vertebral levels. This is largely due to the fact that the pedicles of adjacent vertebrae are not themselves directly adjacent, thus the need for the bar to interconnect the pedicle screws inserted into the vertebrae.

Still another drawback is that the holding power of pedicle screws greatly depends on the length and size of screw used. Increasing the length and size of a screw improves its holding power. However, as discussed above, using such screws that extend through the pedicle on into the vertebral bodies results in a more invasive and time-consuming procedure.

Furthermore, under normal circumstances, intervertebral discs support approximately 70-80% of axial loads imposed upon the lumbar spine, whereas the rest of such axial loads fall on spinal structures including, among others, the facet joints. As a rule, natural distribution of axial loads is, however, disturbed as a result of implantation surgery. Typically, the pedicle screws carry axial loads in excess of 20-30%. One of the reasons for such a deviation from the natural distribution is the concern that unless the vertebral motion segment to be fused is not adequately immobilized, fusion will not occur. As a result, rigid stabilization systems are necessary for the initial healing. Hence, the pedicle screws, viewed as a structure, which is capable of supporting greater axial loads, are characterized by intentionally massive configurations capable of extending through the vertebral bodies of the adjacent vertebrae. Once fusion has occurred, the extensive pedicle screw hardware is usually left in the patient. There is concern that leaving so much 'foreign' material behind could be detrimental to the patient. Finally, there is also a concern that existing pedicle screw systems may in fact be more rigid than necessary for a fusion to occur, and that a less rigid system that allows more 'normal' load sharing conditions may be preferable.

It is, therefore, desirable to provide a bone fastener configured to couple the facets of the adjacent vertebrae to be fused or bone fragments of the bone to be fixed and have a simple and reliable structure capable of stabilizing the adjacent facets during fusion or bone fragments.

SUMMARY OF THE INVENTION

Consonant with the objectives of the present invention, the inventive fastener is configured to fuse the facet joints bridging adjacent superior and inferior vertebrae.

In accordance with one aspect of the invention the inventive fastener is configured to penetrate through the facet joints between the inferior articular process of the superior one of the adjacent vertebrae and the superior articular process of the inferior vertebra. Several embodiments of such an inventive fastener are disclosed.

According to one embodiment, the inventive fastener includes an expandable portion formed on its body and capable of extending radially outwards. Engagement of the fastener with the bone may be a result of external force acting upon the expandable potion so as to provide its radial outward expansion. Alternatively, such an expansion is due to the physical characteristics of material from which the fastener is made. The fastener advantageously is configured so as to have its distal end terminate within base of the superior articular process of the inferior vertebra without further penetration on into the vertebral body thereof.

In accordance with another aspect of the invention, the fastener is configured to engage the facets of the adjacent vertebrae without actually penetrating through the facet joint. In accordance with one embodiment, the fastener has a pair of engaging jaws linearly expandable relative to one another to clamp the opposite surfaces to be engaged. Alternatively, the fastener is configured to have its engaging jaws displaceable angularly relative to one another.

It is, therefore, an object of the invention to provide a fastener configured to have a structure providing for a less invasive and less time consuming procedure directed to stabilizing adjacent vertebrae.

Still another object of the invention is to provide a fastener configured to have a simple structure ensuring its easy placement through the facets or surrounding the facets of the vertebrae to be fused.

Yet another object of the invention is to provide a fastener configured for use in a percutaneous procedure used as supplemental posterior stabilization in a circumferential or 360 degree fusion or as a stand-alone device for cases with slight posterior instability.

BRIEF DESCRIPTION OF THE DRAWINGS

The above and other objects, features and advantages will become more readily apparent from the description of preferred embodiments disclosed with reference to the accompanying drawings, in which.

DETAILED DESCRIPTION OF PREFERRED EMBODIMENTS

Figure 1:
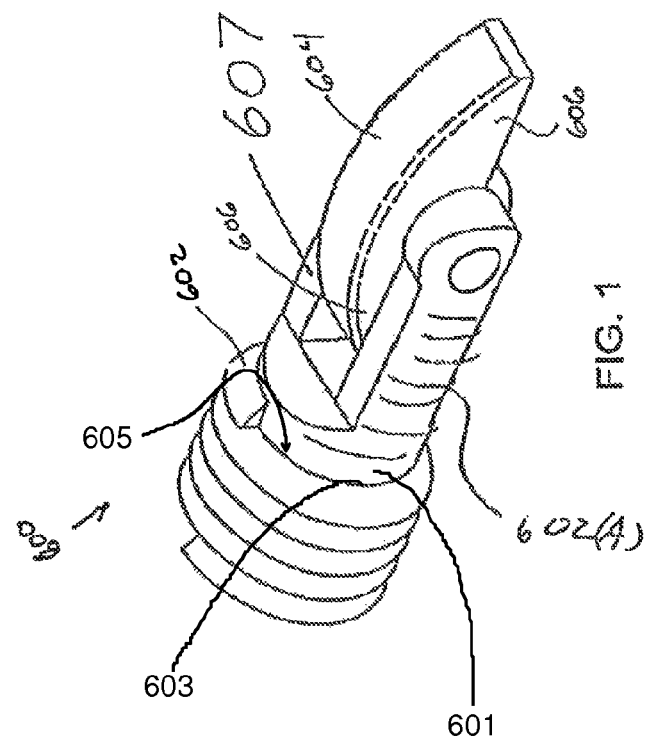
FIG. 1 is a perspective view of a bone fastener in accordance with another embodiment of the present disclosure.

Referring to FIGS. 1 to 24, numerous embodiments of the inventive fastener can be successfully used in a variety of spinal implantation methods and is configured as a stabilization device directed to either secure bone segments or connect inferior and superior articular processes of superior and inferior adjacent vertebrae, respectively. In the latter, the rivet assembly can be used as supplemental posterior stabilization in a circumferential or 360 degree fusion or as a stand-alone device for cases with slight posterior instability.

A few methods of securing bone fragments or stabilizing the facets can be employed in association with the inventive assemblies. In the context of the facet stabilizing procedure, one of the methods provides for forming a small midline incision configured to expose the facets. Then, the inferior articular process of the superior vertebrae, the facet joint and the superior articular process of the inferior vertebrae are drilled so that a drilled path ends at the base of the superior articular process. Accordingly, while the upper cortical surface of the superior articular process is penetrated, the drilled hole does not pass into the pedicle of the inferior vertebra. The hole is dimensioned to be slightly larger than the diameter of each shank of the fastener to allow the latter to be easily guided into the inferior vertebra. Furthermore, other methods such as transfacet, translaminar, etc. can also benefit from utilizing the inventive fasteners.

It is further envisioned to use a percutaneous approach, in which the intended area of penetration is stabbed so as to form a small incision extending substantially vertically from the skin surface to, for example, the posterior surface of the inferior articular process of the superior vertebra. The stabbed hole is smaller than the outer dimension of the fastener and can be expanded either gradually or in a single-step operation by means of a series of dilators or sleeves or, of course, a single sleeve, respectively. Following the expansion of the stabbed hole, the dilator can serve as a guide for a variety of bone-treating instruments including the inventive fasteners.

Yet a further approach allows for surrounding outer surfaces of the bone fragments or the inferior and superior articular processes of the adjacent vertebrae by the inventive fasteners without forming a hole therein. This method includes an adjustable structure allowing the inventive fasteners to engage opposite outer segments of the fragmented bone.

Depending on the given circumstance, either of the above mentioned methods can provide for forming either a blind hole or a throughgoing hole. Accordingly, some of the inventive fasteners can be used exclusively with only the blind or throughgoing hole, whereas the others fasteners are configured for use with both types of the hole. Also, as mentioned above, the inventive fasteners could be used with other components (i.e., plates, etc.), in other locations, and applications (i.e., trauma, etc.).

After the blind or throughgoing hole has been drilled, the surgeon selects a bone fastener shown in FIGS. 1-24 based on their shapes, body length and diameters, head diameters, etc. It is envisioned to provide a surgical kit assembled of a plurality of differently shaped and sized bone fasteners and; optionally, of fastener drivers that can be successfully used in a variety of surgical procedures, as well as an instrumentation case. The number and geometry of the fasteners can vary depending on the material properties of the fastener body and the particular technique and manner of deformation desired to secure the fasteners in and around the facets.

Common to all of the below-disclosed bone fasteners is a structure, which is substantially less rigid than the structure of pedicle screw. The less rigid construct, in turn, leads to more proper (normal) distribution of axial loads between a spinal implant and facet supporting or stabilizing device. In the context of spinal surgeries, in contrast to an implantation procedure associated with four pedicle screws, the inventive procedure may employ only two fasteners having a size smaller than the pedicle screws. Accordingly, the inventive procedure is substantially less invasive than the procedure widely practiced today.

Depending upon the severity of the problem confronted by the surgeon, a bone to be fixed requires differently dimensioned and, of course, differently shaped fasteners. Common to many of the below-disclosed fasteners is an adjustable structure allowing for variations in the overall length of the bone fasteners. Accordingly, as will be particularly disclosed in reference to FIGS. 1-18, instead of custom-made fasteners specifically designed for a given patient, the dimensions of the inventive fastener can be controllably adjusted in accordance with the specifics of the anatomical structure to be fixed. Configuration of the inventive fasteners depends on whether a throughgoing hole or a blind hole is formed in bone fragments or adjacent facets. The fasteners, illustrated in FIGS. 1-6, 18 and 21-22, can be used in fixing the bone fragments provided with both throughgoing and blind holes. FIGS. 7-13 illustrate the inventive fasteners that can be used with throughgoing holes, whereas the fasteners shown in FIGS. 14-17, are configured to surround the bone fragments.

If the fasteners, as shown in FIGS. 1-13 and 18-24 are used in a spinal surgery as a structure for stabilizing the facets of the adjacent vertebrae, the method provides for the insertion of the inventive fastener inserted through the inferior articualr process of the superior vertebra, across the facet joint on into the superior articular process of the inferior vertebra. FIGS. 14-17 illustrate the inventive clamp configured to clamp the posterior surface of the inferior articular process of the superior vertebra and the anterior lateral surface of the superior articular process of the inferior vertebra.

Figure 2:
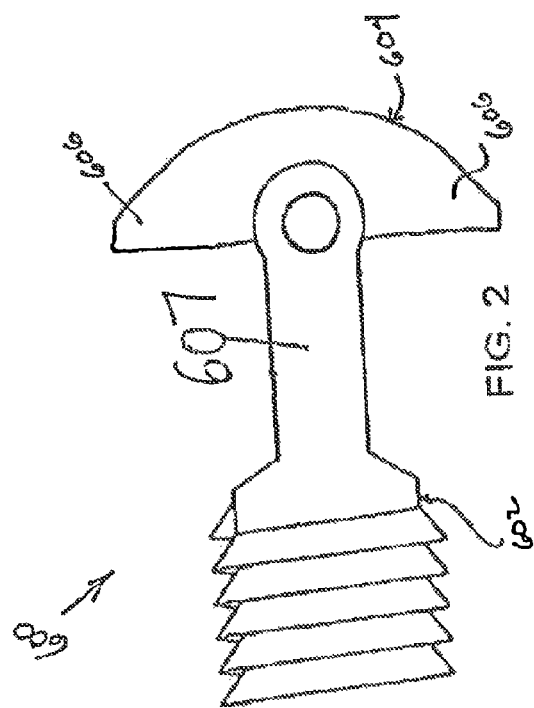
FIG. 2 is a side elevational view of the bone fastener of FIG. 1 shown with the fastening mechanism rotated into its fastening position.

Turning now to FIGS. 1 and 2, a bone fastener in accordance with one embodiment of the disclosure is generally shown as 600. Bone fastener 600 includes a threaded body portion 602 and a shank portion including a pair of spaced arms 607, which pivotally support an anchor 604. Anchor 604 is pivotable from a first insertion position (see FIG. 1) to a second anchoring position (see FIG. 2). Anchor 604 is dimensioned such that when anchor 604 is in the insertion position and opposite ends 606 are aligned with one another along a longitudinal axis of body portion 602, anchor 604 does not project radially beyond the outer diameter of body portion 602. However, when anchor 604 is in the anchoring position, its opposite ends 606 are aligned along an axis extending perpendicular to the longitudinal axis and beyond the diameter of body portion 602 and the diameter of holes formed in the vertebral facets or bone fragments.

In use with the spinal fusion surgery, anchor 604 is inserted through a pair of co-axial holes formed in a pair of vertebral facets, and then fastener 600 is rotated so that threaded body portion 602 enters the holes until anchor 604 has cleared through the hole sufficiently to permit anchor 604 to be rotated to its anchoring position. Once anchor 604 is rotated to its anchoring position, the entire body portion 602 is rotated in an opposite direction to back fastener 600 out of the holes formed in the facets thereby drawing and locking anchor 604 against the surface of the facets. The fastener 600 may be formed as a one piece body or include the shank portion including shanks 602A threadingly or press-fittingly received in a cavity 605 of the body portion 602. The shanks 602A have a textured outer surface 601, and body portion 602 provided with an inner textured surface 603 engaging the outer surface 601 of the shanks 602A. Inner textured surface 603 defines cavity 605 configured for disposal of outer surface 601 of shanks 602A. The textured surfaces 601, 603 may have meshing threads, annular ribs or any formations, configured to improve frictional contact between the body portion 602 and the shanks 602A.

Figure 4:
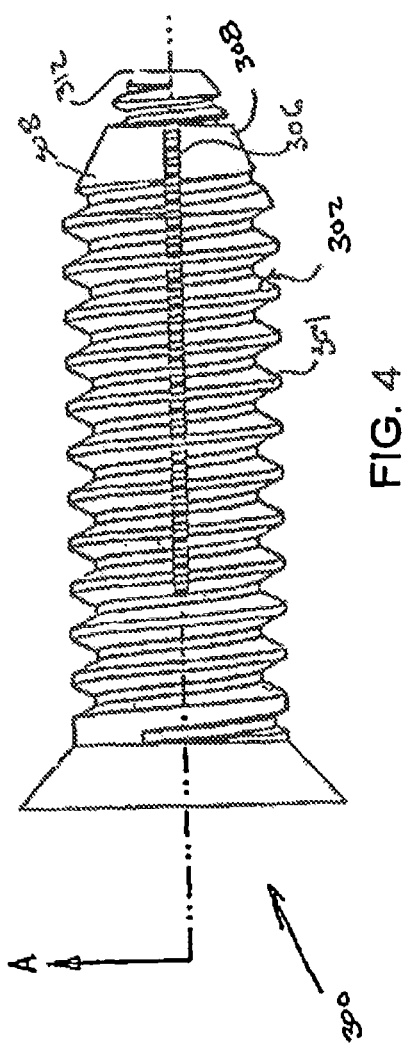
FIG. 4 is a side elevational view of the bone fastener shown in FIG. 3.
Figure 5:
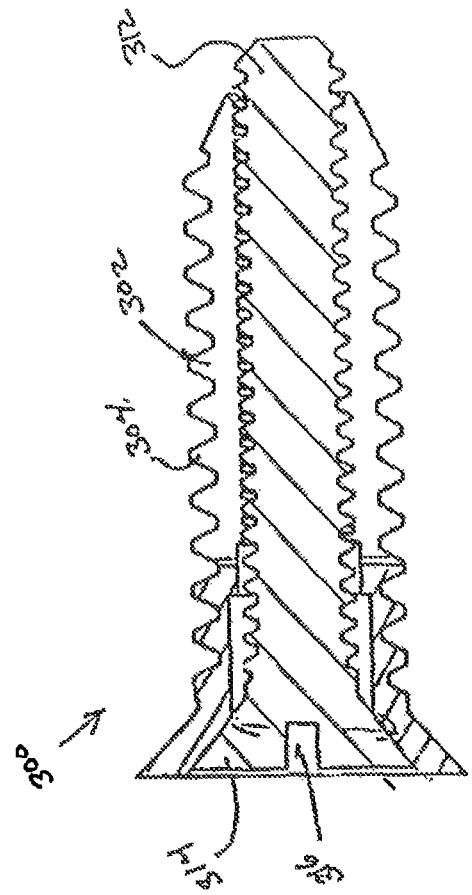
FIG. 5 is a sectional view of the bone fastener shown in FIG. 4 taken along the longitudinal axis.
Figure 3:
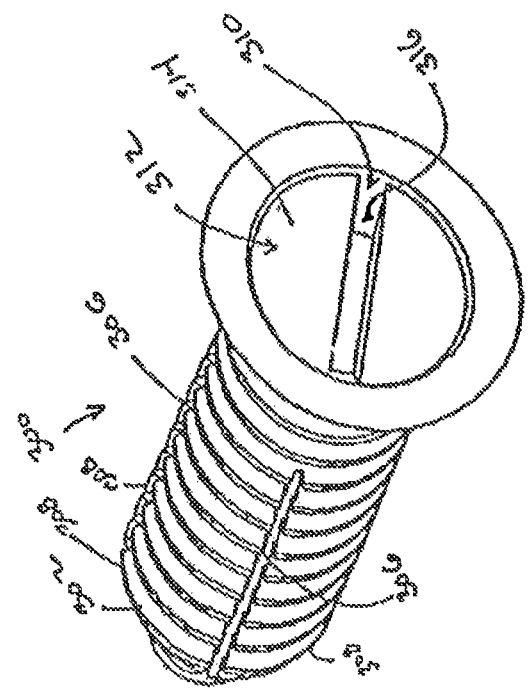
FIG. 3 is a perspective view of bone fastener in accordance with an alternate embodiment.

As shown in FIGS. 3-5, bone fastener 300 includes an outer threaded sleeve 302 having threads 304 formed on its opposite outer surface and inner tapered surface, a plurality of radial slits 306 on a distal tip of sleeve 302 and an opening 310 formed in a proximal head thereof The slits 306 extend from a proximal end of sleeve 302 and define a plurality of legs 308. Fastener 300 further includes a screw 312 configured and adapted to be threadingly received in opening 310 of sleeve 302. Screw 312 includes a head 314 having a slot or any other opening 316 for assisting in rotational or linear insertion of screw 312. In this manner as screw 312 engages and enters sleeve 302, screw 312 presses against the inner surface of each leg 308 and presses them radially outward from one another. In so doing, threads 304 of sleeve 302 press into and engage against the inner surface of a hole formed in the facets of a vertebrae thereby locking fastener 300 into place and securing the facets to one another.

Figure 6:
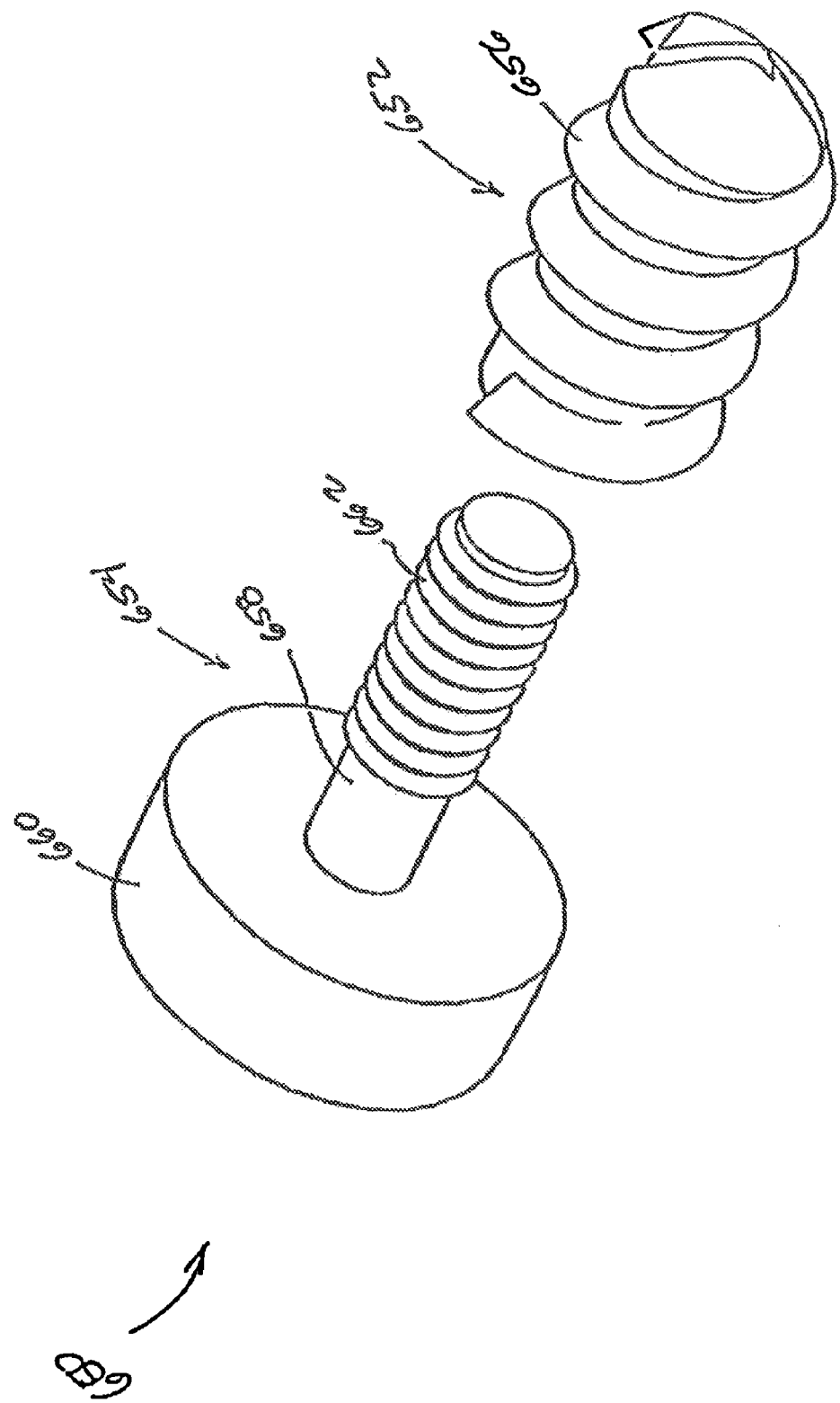
FIG. 6 is an exploded perspective view of a bone fastener in accordance with an alternative embodiment of the present disclosure.

As seen in FIG. 6, a bone fastener, in accordance with an alternative embodiment of the present disclosure, is generally shown as 650. Fastener 650 includes a threaded anchoring portion 652 and a securing portion 654. Anchoring portion 652 includes an outer thread 656 formed thereon and a recess (not shown) formed in a proximal end thereof. Securing portion 654 includes a shaft 658 having a head 660 formed at a proximal end thereof and a series of concentric annular ribs 662 formed at a distal end thereof. Annular ribs 662 are configured and adapted to be received in the recess formed in the proximal end of anchoring portion 652 and to securely hold securing portion 654 in place.

In use, anchoring portion 652 is embedded, through coaxial holes formed in adjacent vertebral facets, such that anchoring portion 652 is imbedded in a second of the pair of facets. With anchoring portion 652 in place, shaft 658 of securing portion 654 is inserted through the hole in a first of the pair of facets and securely received in the recess formed in anchoring portion 652. The base surface of head 660 can be roughened to better grip the outer surface of a facet. While annular ribs have been disclosed, it is envisioned that threads can be provided in place thereof.

Figure 7:
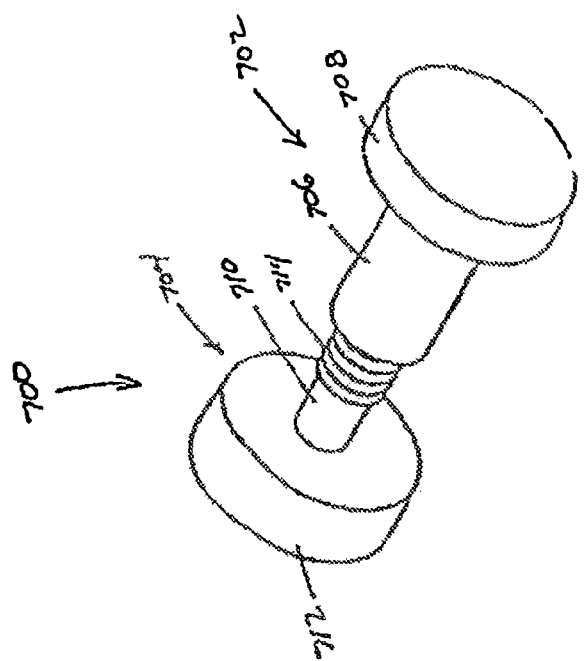
FIG. 7 is an-perspective view of a bone fastener in accordance with another embodiment of the present disclosure.
Figure 8:
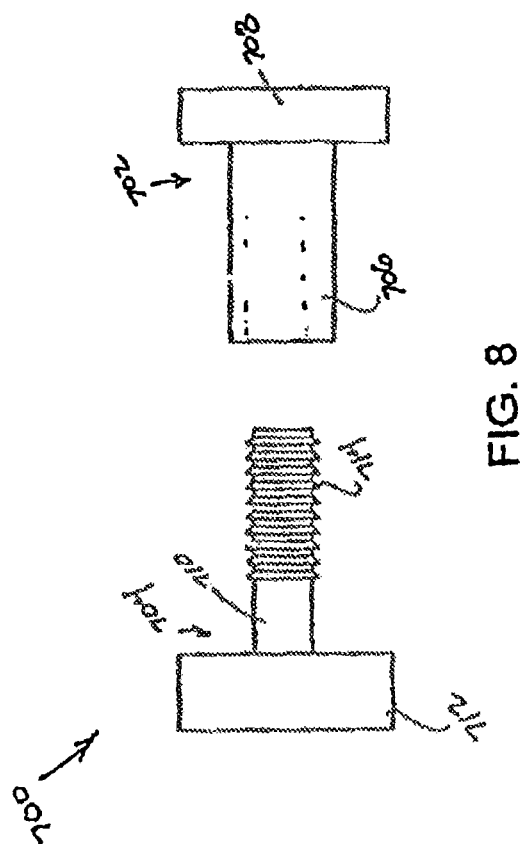
FIG. 8 is a side view of the bone fastener in accordance FIG. 7.

Turning now to FIGS. 7 and 8, a bone fastener in accordance with an alternative embodiment of the present disclosure is shown generally as 700. Fastener 700 includes a first body portion 702 and a second body portion 704. First body portion 702 includes a sleeve 706 having an enlarged head 708 formed at a distal end thereof and a recess (not shown) formed in a proximal end thereof. Second body portion 704 includes a shaft 710 having an enlarged head 712 formed at a proximal end thereof and a series of annular ribs 714 formed at a distal end thereof, wherein ribs 714 are configured and adapted to be inserted into the recess first body portion 702, which recess is configured and adapted to securely receive ribs 714 therein. In use, sleeve 706 is inserted into a pair of co-axial holes formed in a pair of adjacent vertebral facets until enlarged head 708 contacts the outer surface of one of the facets. Shaft 710 of second body portion 704 is inserted, from an opposite direction as compared to sleeve 706, into the co-axial holes formed in the pair of facets and into the recess formed in the end of sleeve 706 until enlarged head 712 contracts the surface of the facet and until second body portion 704 is securely coupled to first body portion 702, thereby securing the pair of facets to one another. The ribs 414 may be easily replaced by outer threads meshing with inner threads which are formed on the inner surface of the sleeve 706.

Figure 9:
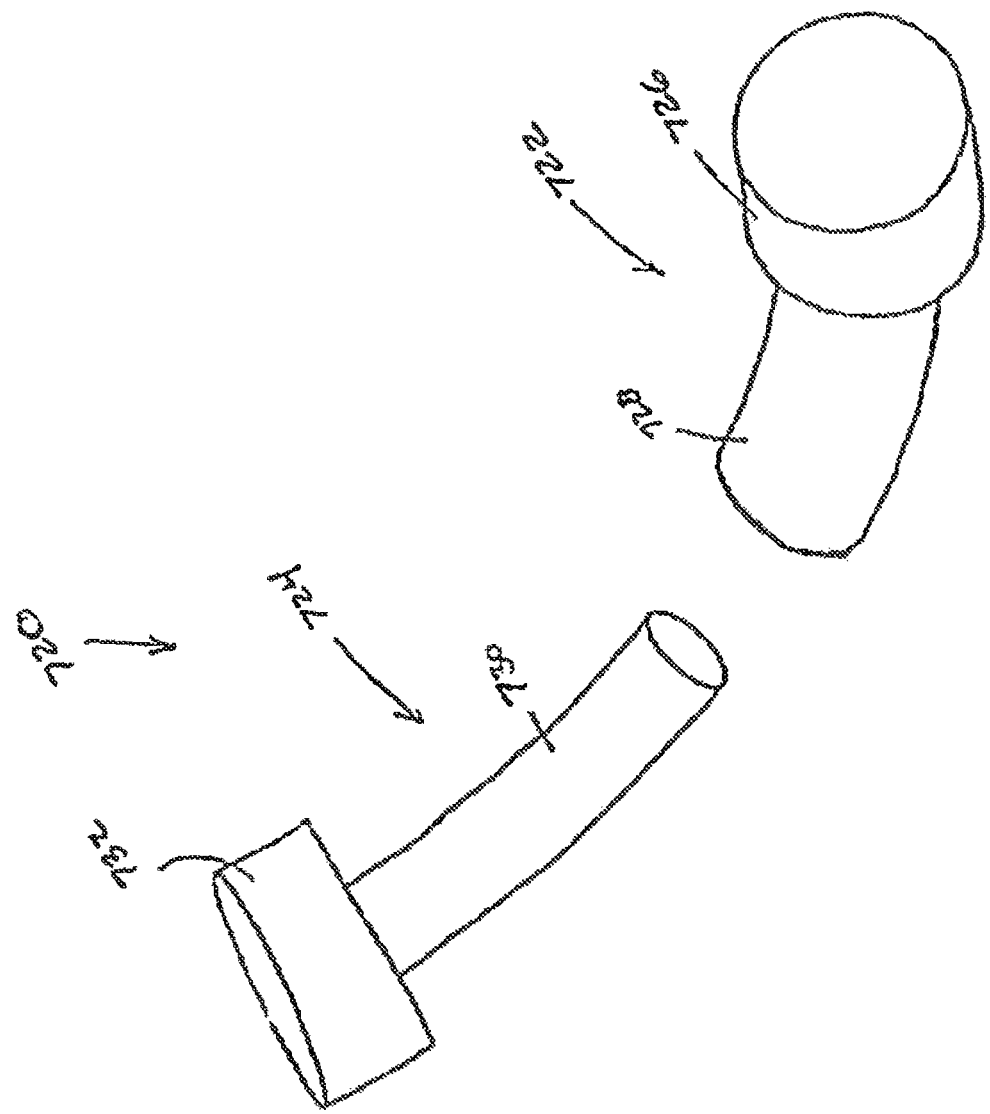
FIG. 9 is an exploded perspective view of a bone fastener in accordance with another embodiment of the present disclosure.

Turning now to FIG. 9, a bone fastener, similar in form and operation, to bone fastener 700 is generally shown as 720. Like bone fastener 700, bone fastener 720 includes a first body portion 722 and a second body portion 724. First body portion 722 includes a curved sleeve 728 having an enlarged head 726 formed at one end and a recess (not shown) formed in an opposite end thereof. Second body portion 724 includes a curved shaft having an enlarged head 732 formed at one end and configured at a second end to be received in the recess formed in first body portion 722. The use of fastener 720 is the same as the use of fastener 700. Outer and inner surfaces of the curved sleeve 728 of the first portion as well as the outer surface of the curved shaft of the second portion 724 can be roughened or textured to improve engagement between the first and second portions and between the first portion and the bone.

Figure 10:
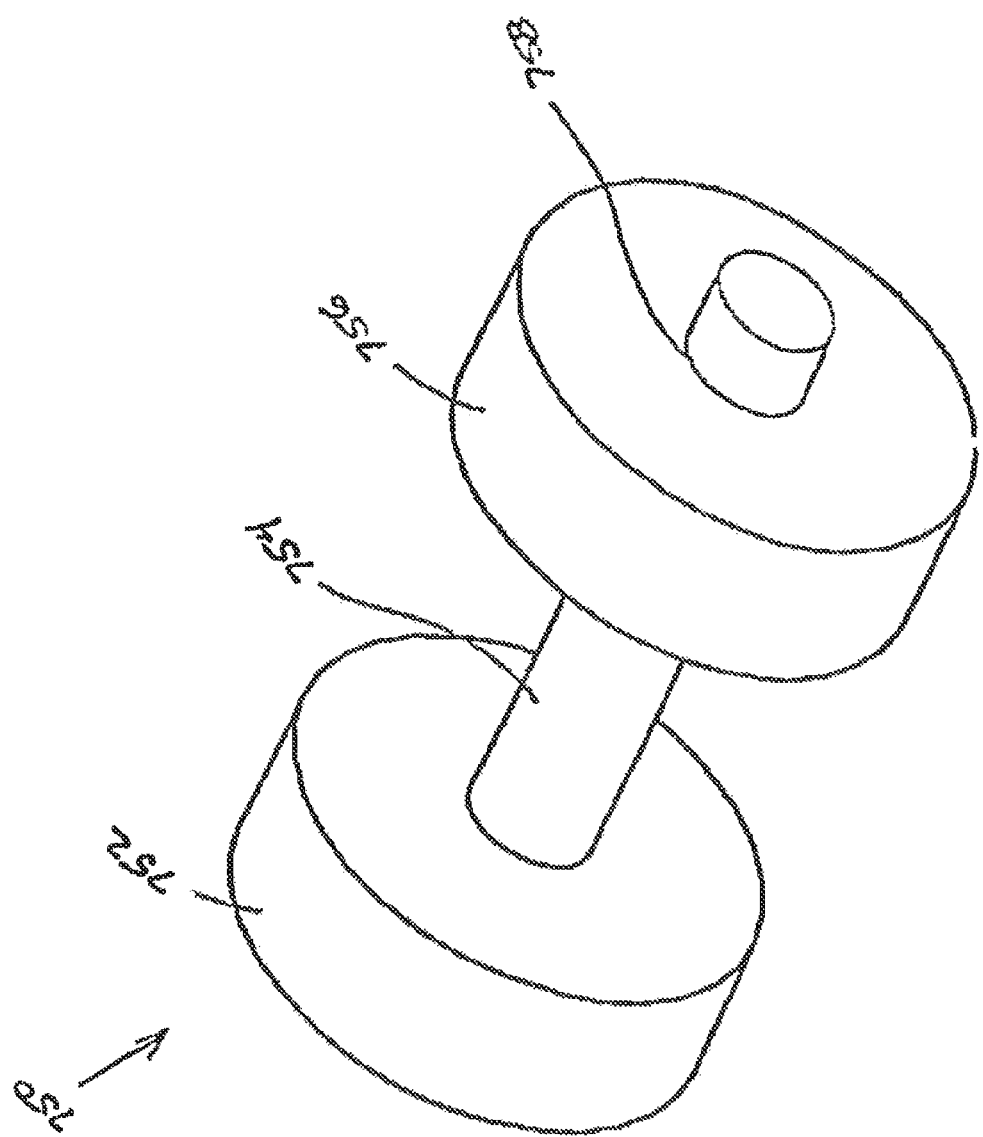
FIG. 10 is a perspective view of the bone fastener in accordance with still another embodiment of the invention.

Turning now to FIG. 10, a bone fastener in accordance with an alternative embodiment of the present disclosure is shown generally as 750. Bone fastener 750 includes stopper 752 having a shaft 754 extending from a distal surface thereof and a collar 756 having a hole 758 formed therethrough. Hole 758 has an inner diameter slightly larger than an outer diameter of shaft 754 such that shaft 754 is tightly secured in hole 758. It is envisioned that the surfaces of stopper 752 and collar 756 which are to contact the surface of the facets are roughened in order to provide increased gripping between fastener 750 and the surface of each facet. In use, shaft 754 is threaded through a pair of co-axial holes formed in a pair of adjacent vertebral facets until the distal tip of shaft 754 extends therefrom. Collar 756 is then press fit onto the distal end of shaft 754 until collar 756 contacts and securely fastens the pair of facets to one another.

Figure 11:
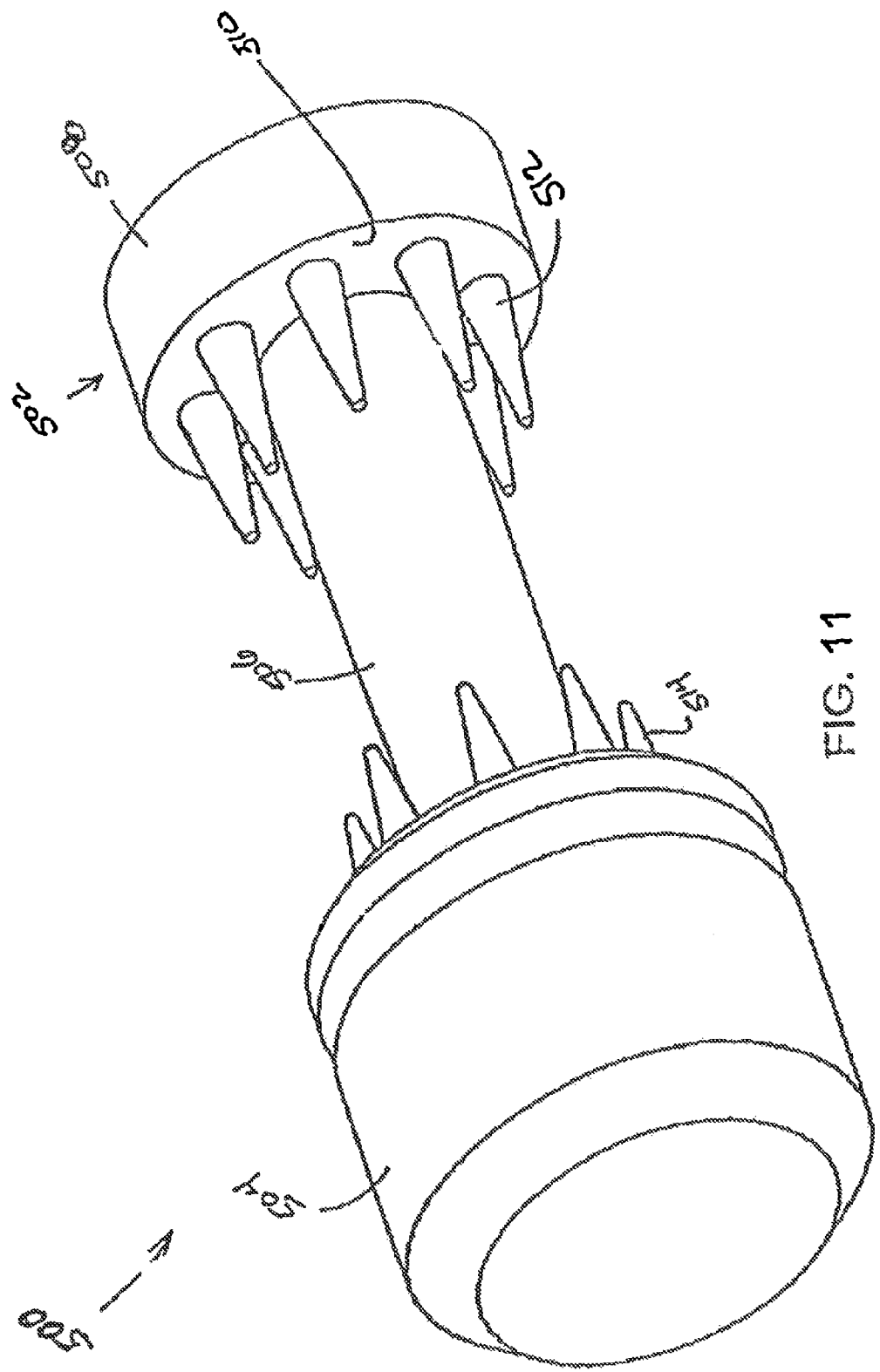
FIG. 11 is a perspective view of a bone fastener in accordance with another embodiment of the present disclosure.

Turning now to FIG. 11, a bone fastener in accordance with an alternative embodiment of the disclosure is generally shown as 500. Bone fastener 500 includes a first fastener portion 502 and a second fastener portion 504. First fastener portion 502 includes a mid-shaft 506 having an enlarged head 508 formed at a distal end thereof, wherein enlarged head 508 has a larger diameter than mid-shaft 506 thereby defining a shoulder 510 therebetween. A plurality of spikes 512 are formed on shoulder 510 and are configured and adapted to dig into the surface of a facet. Second fastener portion 504 is provided with a recess (not shown) for receiving a proximal end of mid-shaft 506 and a plurality of spikes 514 formed around the periphery of the recess. Second fastener portion 504 is provided with a spring loaded release mechanism configured and adapted to receive the proximal end of mid-shaft 506 and to retain mid-shaft 506 within the recess of second fastener portion 504. In use, mid-shaft 506 of first fastener portion 502 is inserted through a pair of co-axial holes formed in a pair of adjacent facets until spikes 512 contact the outer surface of the facet and until the proximal end of mid-shaft 506 projects out of the pair of co-axial holes. Then, second fastener portion 504 is pressed onto the proximal end of mid-shaft 506 such that the spring loaded release mechanism securely retains the proximal end of mid-shaft 506 within the recess formed in second fastener portion 504.

Figure 12:
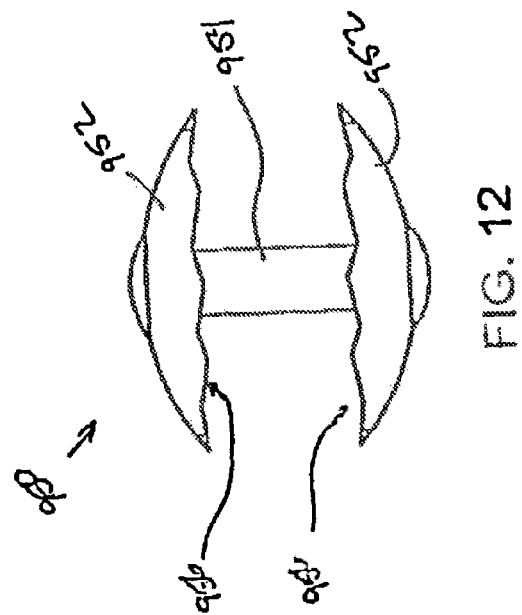
FIG. 12 is a side view of the bone fastener configured with a further embodiment of the invention.
Figure 13:
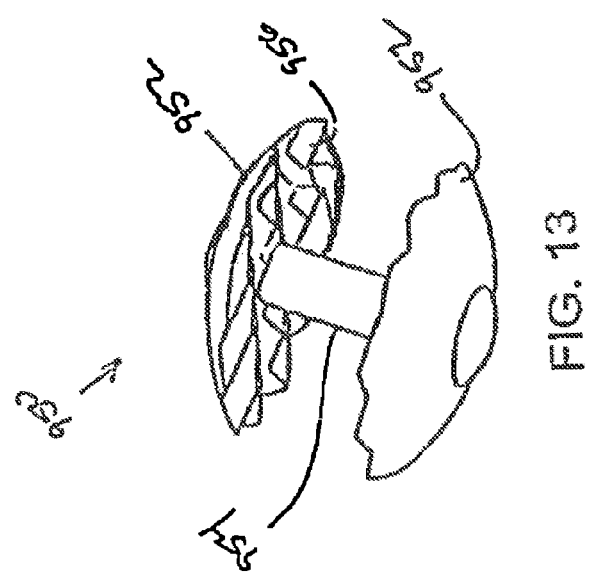
FIG. 13 is a perspective view of the bone faster of FIG. 12.

Turning now to FIGS. 12 and 13, a bone fastener in accordance with an alternative embodiment of the present disclosure is shown generally as 950. Fastener 950 includes a pair of washers 952 interconnected by a shaft 954. Each washer 952 is, generally hemispherical and includes a roughened inner surface 956 to better grip an outer surface of a facet. Shaft 954 may be a threaded shaft configured and adapted to engage a threaded recess formed in the inner surface of each washer 952 or configured and adapted to pass completely through each washer 952 and receive a nut (not shown) on either end thereof or any number of various means for coupling each washer 952 to shaft 954.

Figure 14:
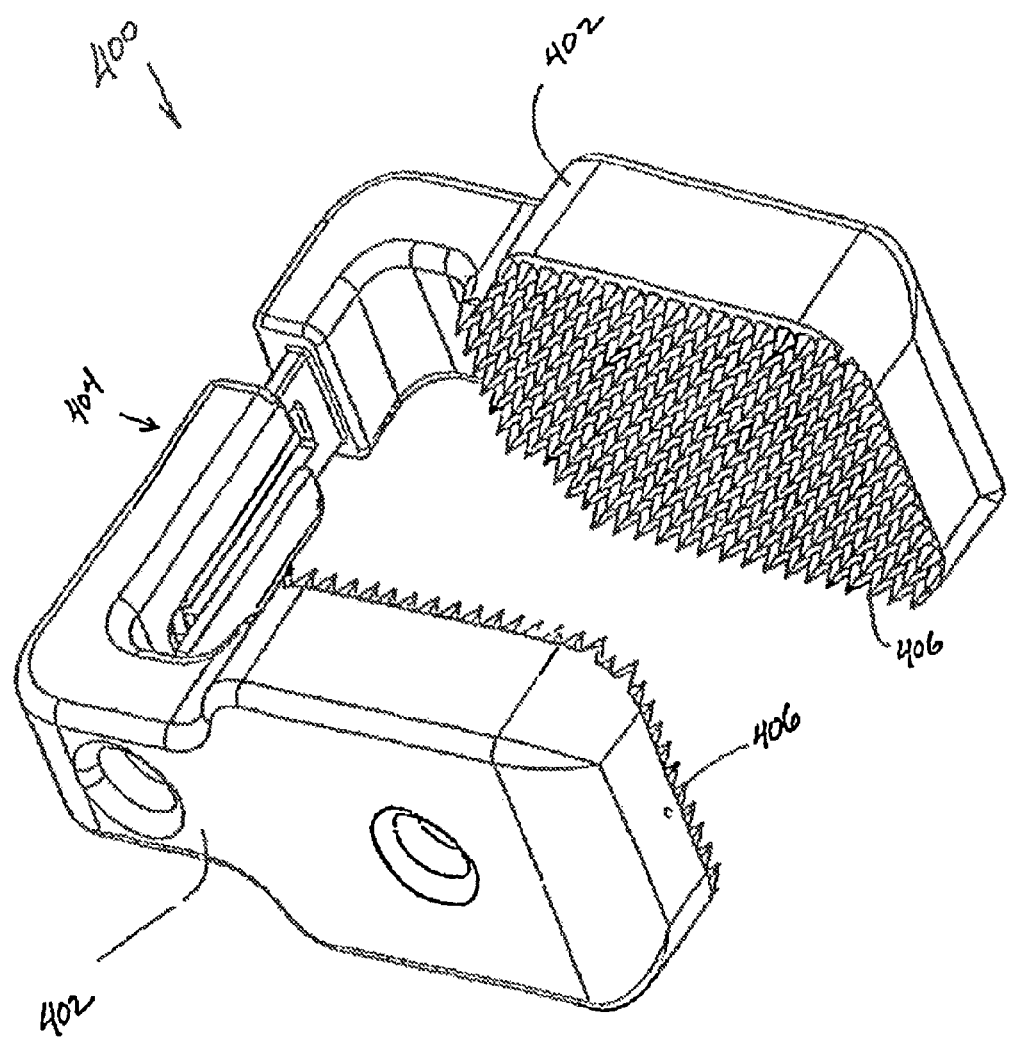
FIG. 14 is a perspective view of a bone fastener in accordance with an alternate embodiment of the present disclosure.

In FIG. 14, a bone fastener clamp is generally shown as 400. Clamp 400 includes a pair of jaws 402 interconnected by a ratchet mechanism 404. Each jaw 402 includes an inner surface having a plurality of teeth 406 formed thereon for grabbing the surface of the facets and preventing clamp 400 from sliding off of a pair of facets. In use, clamp 400 is opened such that jaws 402 are spaced at a maximum distance from one another, clamp 400 is then placed around a pair of facets and ratchet mechanism 404 operated such that the pair of jaws 402 are drawn in toward one another until the pair of facets are secured to one another. Displacement of the jaws continues until the teeth 406 are deformed. The locked postions While teeth 406 have been disclosed; it is envisioned that the inner surface of jaws 402 can be roughened to thereby grab and hold the outer surfaces of the facets.

Figure 15:
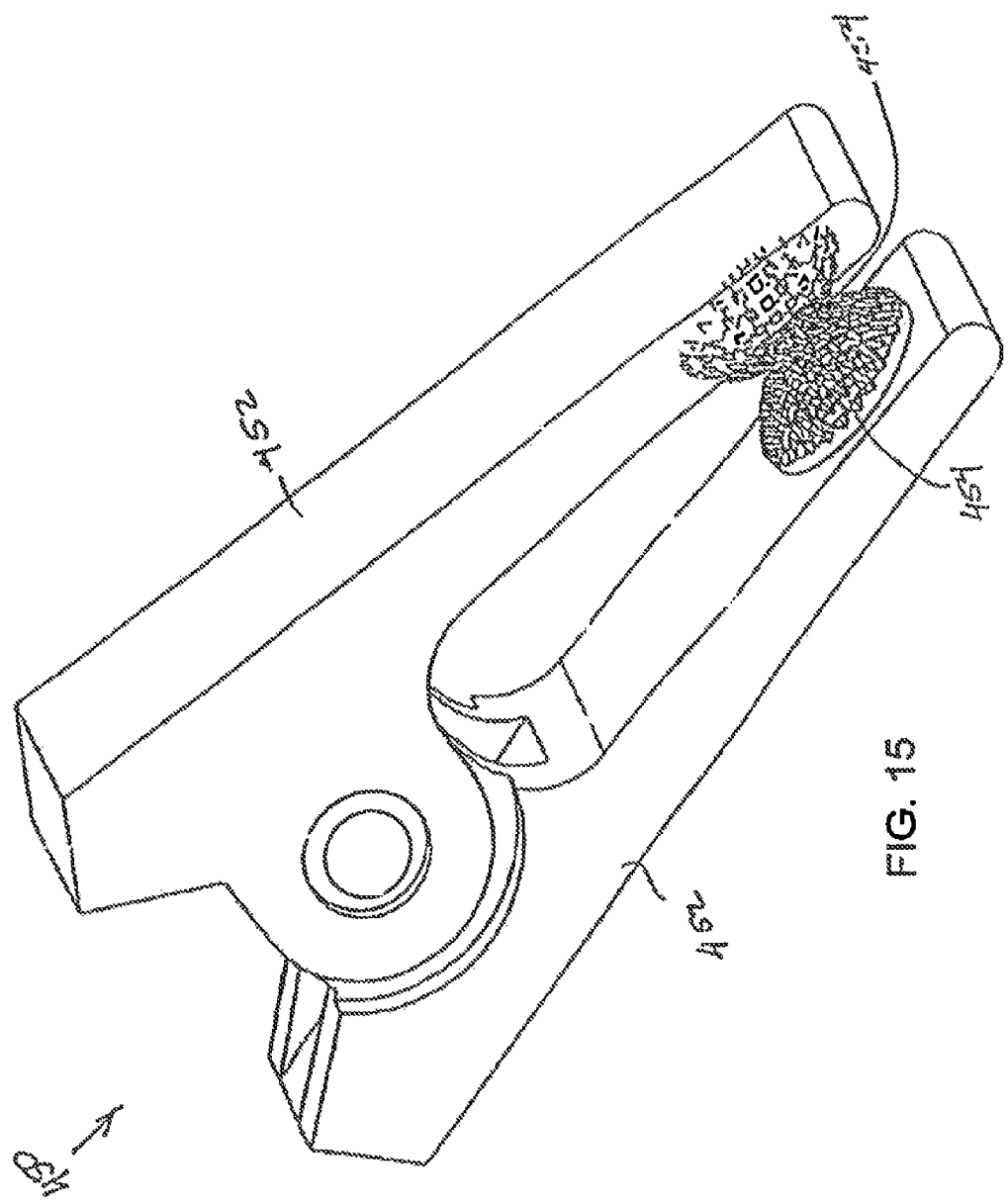
FIG. 15 is a perspective view of a bone fastener in accordance with another embodiment of the present disclosure.

Turning now to FIG. 15, a bone clamp in accordance with an alternative embodiment is shown generally as 450. Clamp 450 is generally a clothespin like structure including a pair of jaws 452 spring biased to a closed position in which the distal end of jaws 452 contact one another. Each inner surface of the distal end of jaws 452 is provided with teeth/roughened surface 454 which is configured and adapted to grab a pair of facets therebetween.

Figure 16:
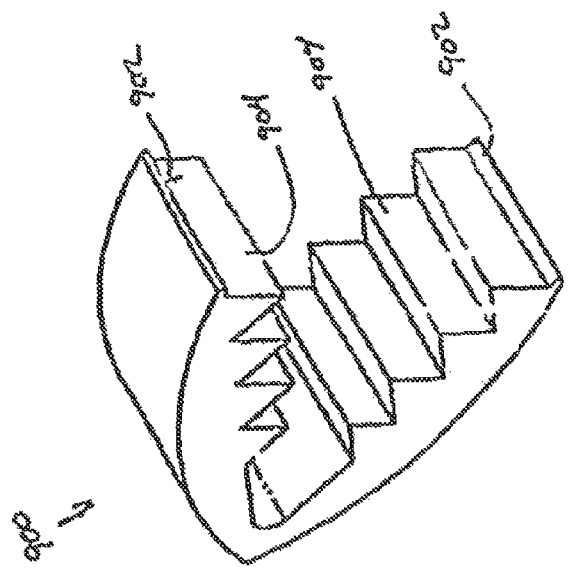
FIG. 16 is a perspective view of a bone fastener in accordance with yet another embodiment of the present disclosure.
Figure 17:
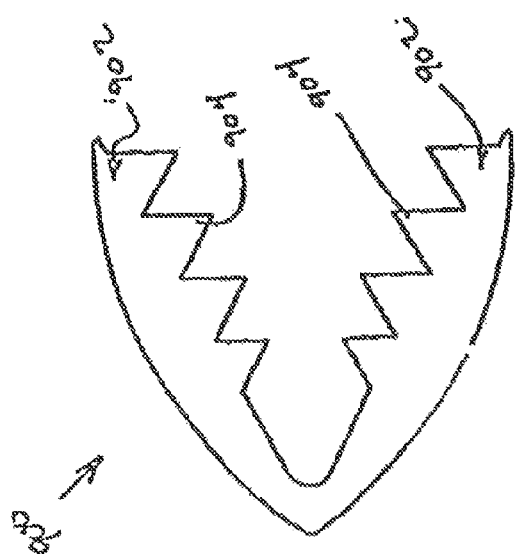
FIG. 17 is a side view of the bone fastener shown in FIG. 16.

In FIGS. 16 and 17, a bone fastening clamp in accordance with an alternative embodiment of the present disclosure is shown generally as 900. Clamp 900 is generally "C" shaped including a pair of jaws 902 joined together at a proximal end thereof and being spaced from one another at a distal end thereof. Each jaw 902 includes a series of teeth 904 formed along an inner surface thereof defining a "V" shaped channel therebetween. In use, a pair of adjacent vertebral facets are brought into contact with one another and the distal end of clamp 900 slid over the pair of facets until the teeth are permanently deformed in a locked position of the clamp. Accordingly, the pair of facets are securely held in place in the "V" shaped channel between the pair of jaws 902.

Figure 18B:
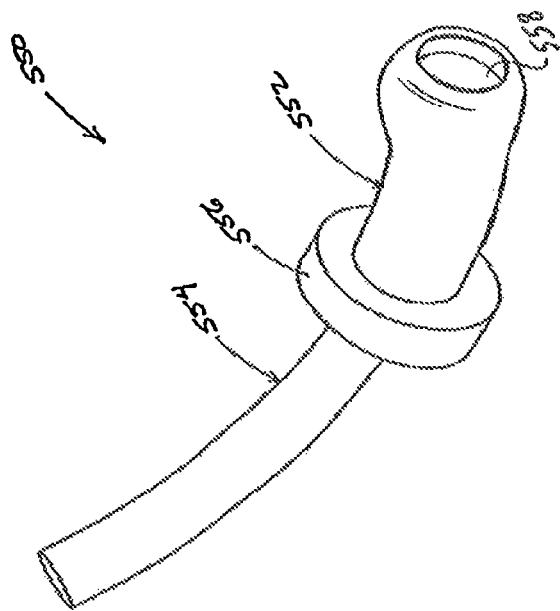
FIG. 18A and 18B are perspective views of the bone fastener with a further embodiment in accordance with the invention.
Figure 18A:
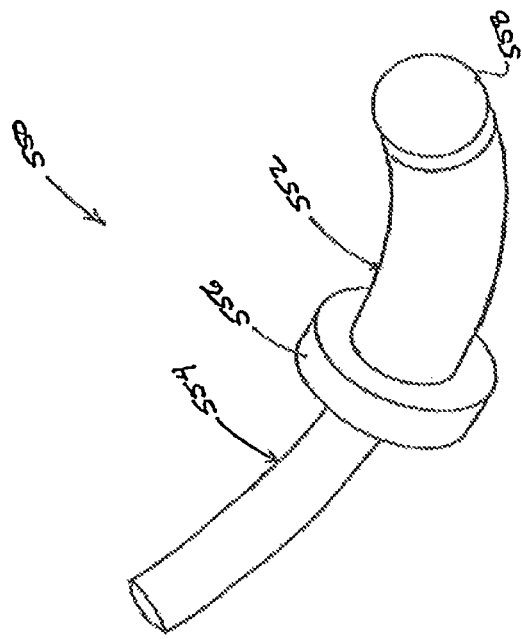

In FIG. 18A, a bone fastener in accordance with an alternative embodiment of the present disclosure is generally shown as 550. Bone fastener 550 is a rivet like structure including a curved cylindrical rivet body 552 and a corresponding curved elongated mandrel 554 slidingly disposed within and extending through rivet body 552. Rivet body 552 includes a collar 556 formed at a proximal end thereof which act as a stop thereby preventing rivet body 552 from passing completely through a pair of co-axial holes formed in a pair of adjacent facets. Mandrel 554 includes an enlarged head 558, which enlarged head 558 deforms the distal end of rivet body 552 when mandrel 554 is pulled through rivet body 552, as illustrated in FIG. 18B. In use, rivet body 552 is inserted through the pair of co-axial holes formed in the pair of facets until collar 556 contacts the surface of the facet and until enlarged head 558 projects out from the second facet. Mandrel 554 is then pulled proximally through rivet body 552 thereby deforming the distal end of rivet body 552 against the surface of the facet and securing the facets to one another.

Figure 20:
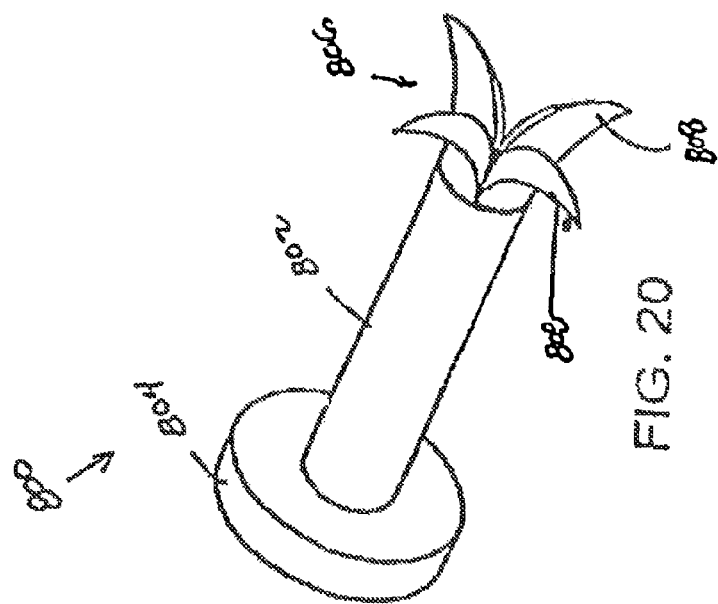
FIG. 20 is a perspective view of the bone fastener of FIG. 19 shown in a deployed position.
Figure 19:
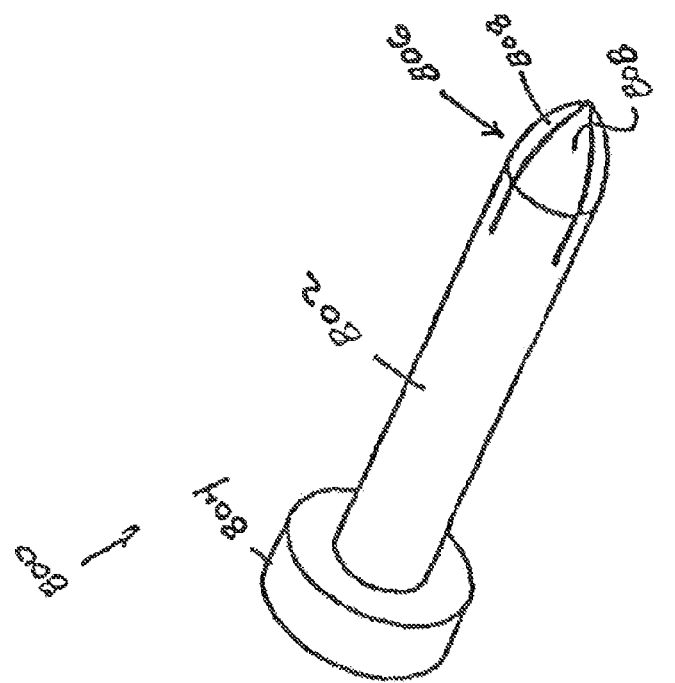
FIG. 19 is a perspective view of a bone fastener in accordance with another embodiment of the present disclosure shown in a rest position.

As seen in FIGS. 19 and 20, a bone fastener in accordance with an alternative embodiment of the present disclosure is shown generally as 800. Bone fastener 800 includes a body portion 802 including an enlarged head 804 formed at a proximal end thereof and an expandable tip 806 formed at a distal end thereof. Distal tip 806 is divided into a plurality of deformable fingers 808. Fastener 800 is made of a shape memory alloy and as such, when fastener 800 is threaded through a pair of co-axial holes formed in a pair of adjacent facets, the heat applied to the fastener causes the deformable fingers 808 of divided, tip 806 to peel away from one another and against the surface of the facet (see FIG. 20). In use, fastener 800 is threaded through the pair of co-axial holes until head 804 contact the surface of the facet and fingers 808 allowed to deform as a result of the heat applied to the fastener 800.

Figure 22:
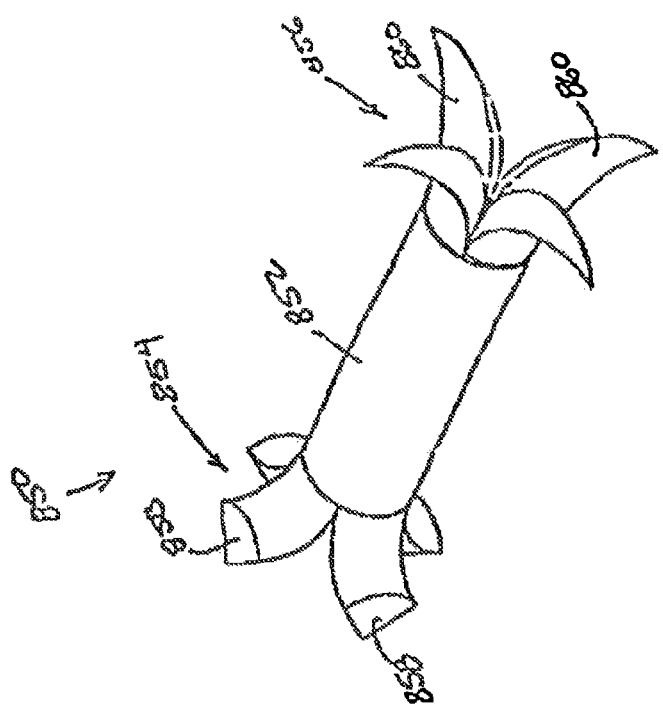
FIG. 22 is a perspective view of the fastener of FIG. 21, but shown in a deployed position.
Figure 21:
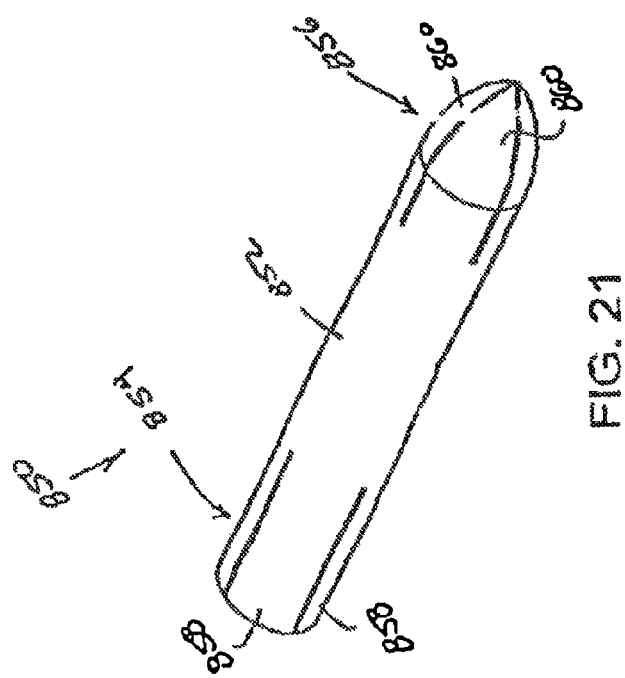
FIG. 21 is a perspective view of the bone fastener in accordance with still another embodiment of the invention and shown in a rest position thereof.

In FIGS. 21 and 22, an alternative embodiment of fastener 800 is disclosed and is shown generally as 850. Fastener 850 includes a body portion 852 having an expandable proximal portion 854 and an expandable distal portion 856. Proximal portion 854 is made up of a plurality of deformable fingers 858 while distal portion 856 is also made up of a plurality of deformable fingers 860. Like fastener 800, fastener 850 is made of a shape memory allow. Thus, in use, distal portion 856 is threaded through a pair of co-axial holes formed in a pair of adjacent vertebral facets and deformable fingers 858 and 860 permitted to deform due to the heat applied to the fastener acting on the shape memory alloy to cause the deformable fingers 858 and 860 to deform radially outward from one another (see FIG. 22). In both fastener 800 and 850, the distal end is in the shape of a bullet in order to facilitate insertion of the fastener into the pair of co-axial holes. In addition, the length of the body portion of each fastener 800 and 850 is selected to ensure that sufficient penetration of the distal tip takes place through the pair of adjacent facets.

As shown in FIGS. 19-22, distal ends of the fasteners are segmented. However, the distal end may have a peripheral score line, which defines a continuous annular end portion of the body of the fastener configured to flare upwards and to engage the inner surface of the bone.

Figure 23:
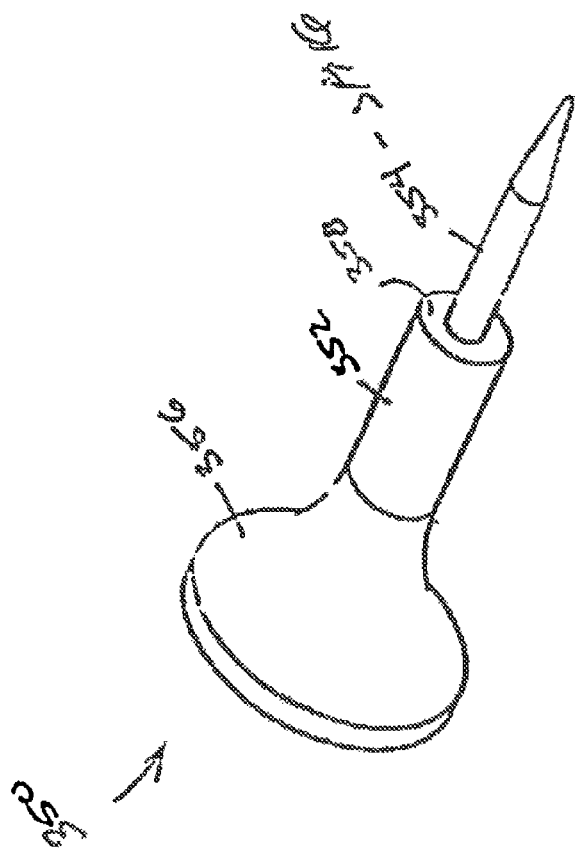
FIG. 23 is a perspective view of the bone fastener of an alternative embodiment of the, invention.

In FIG. 23 a bone tack, in accordance with another embodiment of the present disclosure, is generally shown as 350. Tack 350 includes a cylindrical body portion 352 having an elongated spike 354 projecting outwardly from a distal end thereof and an enlarged head 356 formed at a proximal end thereof. Spike 354 has a smaller diameter than body portion 352, thereby defining a shoulder 358. In use, a first tack is buried into a first site of interest (i.e., a first facet) until spike 354 is completely buried into the first site up to shoulder 358, a second tack is similarly buried into a second site (i.e., a second facet) up to shoulder 358, then a cable/wire (not shown) is wrapped around and between the heads of the tacks thereby preventing a relative motion of the facets with respect to one another. Two or more tacks may be needed to prevent relative motion in other degrees of freedom.

Figure 24:
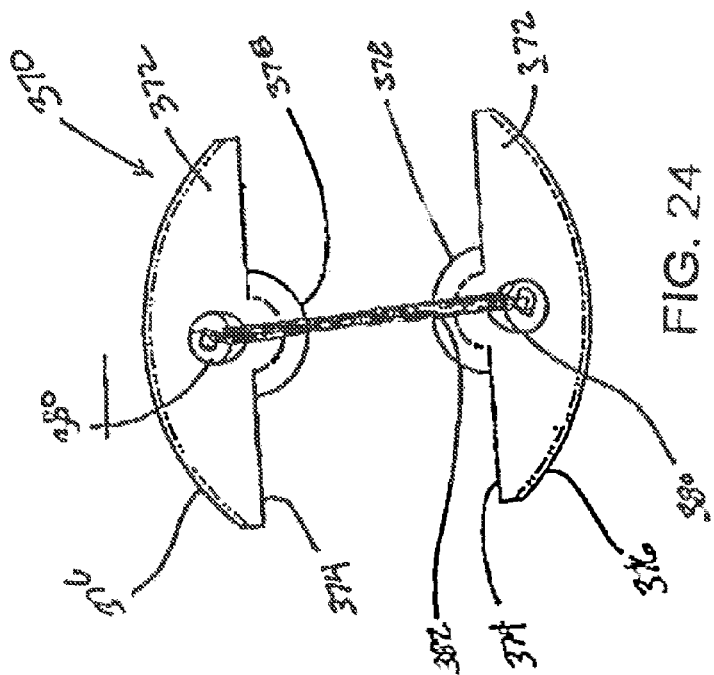
FIG. 24 is a top view of yet another embodiment of the invention.

In FIG. 24 a bone fastener in accordance with an alternative embodiment of the present disclosure is generally shown as 370. Fastener 370 includes a pair of anchors 372 with each anchor 372 having a planar inner surface 374, an arcuate outer surface 376 and a hub 378 projecting outwardly from planar inner surface 374 along a midline thereof. Each anchor 372 includes a through hole 380 formed transversely through the midline thereof. In use, a first anchor is positioned against an outer surface of a facet such that the hub seats within a hole formed in the facet, a second anchor is positioned on the outer surface of an adjacent facet such that its respective hub seats within a hole formed in the adjacent facet, a cable/wire 382 is threaded though the holes in each facet as well as through the holes formed in each anchor and finally wire 382 is pulled tight and the loose ends tied together to thereby secure fastener 370 in place and to secure the adjacent facets to one another.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A fastener for stabilizing multiple bone fragments, comprising:
    a first portion having a threaded outer surface configured to extend through and engage the multiple bone fragments;
    a second portion connected to the first portion defining a longitudinal axis therebetween;
    and
    an anchor pivotally mounted between two spaced apart arms of the second portion, the anchor having a convex upper surface and a planar lower surface configured for engagement with a surface of at least one of the multiple bone fragments,
    wherein the anchor is disposable between a first insertion position such that the planar surface of the anchor is substantially parallel with the longitudinal axis and a second anchoring position such that the planar surface of the anchor is transverse to the longitudinal axis so as to secure the bone segments,
    wherein the first and second portions are displaceable relative to one another to reach a locked position after rotation of the anchor to the second anchoring position.

2. The fastener of claim 1, wherein the first portion has an inner surface defining a cavity, and the second portion extends between a first end pivotally connected with the anchor and a second end having an outer surface disposable in the cavity of the first portion so as to allow displacement of the second portion relative to the first portion to establish a locked position of the fastener, the inner surface of the first portion and the outer surface of the second portion being textured to provide frictional engagement between the first and second portions of the fastener.

3. The fastener of claim 2, wherein the textured inner surface of the first portion includes a plurality of annular ribs or threads.

4. The fastener of claim 1, wherein the first and second portions are monolithically formed.

5. A method for operating a bone fastener used for stabilizing bone fragments, comprising the steps of:
- displacing a first portion of the bone fastener through one of the bone fragments in a first direction;
- displacing a second portion of the bone fastener through the bone fragments in the first direction so as to engage the first and second portions of the fastener;
- displacing the fastener through the bone fragments in a second direction, opposite the first direction to orient an anchor of fastener in an anchoring position; and
- displacing the first and second engaged portions relative to one another to a locked position, wherein the bone fragments are secured by the locked in fastener,
- wherein the anchor is pivotally mounted between two spaced apart arms of the second portion, wherein the first and second portions are displaceable relative to one another to reach the locked position after rotation of the anchor to the second anchoring position.

\* \* \* \* \*